United States Patent [19]

Fox et al.

[11] 4,053,379

[45] Oct. 11, 1977

[54] STARCH DERIVATIVES

[75] Inventors: John Francis Fox; Thomas William Roylance; Angus Campbell Mair, all of Edinburgh, Scotland

[73] Assignee: Arbrook, Inc., Arlington, Tex.

[21] Appl. No.: 621,441

[22] Filed: Oct. 10, 1975

[30] Foreign Application Priority Data

June 20, 1975 United Kingdom ............... 46232/75
Oct. 25, 1974 United Kingdom ............... 46232/74

[51] Int. Cl.$^2$ ................................. B01J 1/10
[52] U.S. Cl. ................................. 204/160.1; 106/214; 21/54 R; 427/36; 427/44; 536/111
[58] Field of Search ............ 204/160.1; 260/233.3 A, 260/233.5; 21/54 R; 427/44, 36; 106/214; 536/111

[56] References Cited

U.S. PATENT DOCUMENTS

| 2,626,257 | 1/1953 | Caldwell et al. | 260/233.3 |
| 2,627,516 | 2/1953 | Lohmar, Jr. | 260/233.3 |

OTHER PUBLICATIONS

Kirk–Othmer, Encyclopedia of Chemical Technology, vol. 18, pp. 817–820 (1969).

*Primary Examiner*—Melvyn I. Marquis
*Attorney, Agent, or Firm*—Alice O. Robertson

[57] ABSTRACT

Starch, in a form so it is absorbable by body tissues and especially suitable for use as a medical dusting powder or lubricant for surgical gloves, is obtained by treating a substituted polysaccharide such as etherified vegetable starch with an acid or alkaline material and heating until it has a reducing power of at least 15 $R_{Cu}$ units, and then optionally is sterilized with gamma-irradiation thereby raising the reducing power to at least 65 $R_{Cu}$ units.

15 Claims, No Drawings

STARCH DERIVATIVES

The present invention relates to derivatives of higher polysaccharides of the starch type and more particularly to such derivatives for use in surgery and medicine in general which are absorbable by, and harmless to, body tissues. Products of the invention are contemplated for instance as lubricants, as dressing materials for textile fibre and as diluents or carriers, mainly but not exclusively in dry, powdered form, especially in a surgical or other medical context. The invention is especially concerned with a medical dusting powder.

Various procedures for treating the human or animal body incur the possibility that material applied in the treatment, whether inherently or incidentally, may enter and remain in the living tissue. It is therefore necessary to ensure that such materials shall be harmless to the tissues and either inert and non-irritant, or satisfactorily absorbable.

One such material is the powder widely used to lubricate surgical gloves. This may be employed in the manufacture of the gloves as a mould lubricant or glove finishing agent, or it may be applied immediately prior to the use of the gloves to prevent adhesion between glove surfaces during steam sterilisation or it may be used by dusting the hands to facilitate putting on the gloves. At one time talc was universally employed for some such purposes but its use was discontinued because it resulted in serious adverse effects where it had entered the tissues from the glove or in other ways. These effects included severe postoperative complications, strong inflammatory reactions and particularly adhesions, peritonitis and granuloma, in cavities surgically operated upon.

The medical dusting powder which has been established over the last 25 years as highly satisfactory in the place of talc, in cases where the dusted article such as the surgical glove, is steam sterilized before use, is the subject of U.S. Pat. No. 2,626,257. It comprises a starch powder in its non-gelatinized state partially etherified to a specified degree, together with about 0.05 to 10 percent of its weight of magnesium oxide. The degree of etherification in the product of the U.S. patent, is that which corresponds to treatment of the starch in aqueous suspension with an agent causing formation of diether linkages wherein chains having more than one carbon separate the oxygen bonds, in an amount sufficient to link 2 to 3 percent of the free hydroxyl groups.

After steam sterilisation, for instance by autoclaving, this etherified starch is readily absorbable by, and harmless to, body tissues.

In more recent years other procedures have come into use for sterilising goods applied surgically, such as sterilisation by means of ethylene oxide or by gammair-radiation. There exists a need for another medical dusting powder of the general type discussed above, and for other starch derivative preparations, which will be acceptable especially in applications where steam sterilisation is not practical or for any other reason not used.

It is a broad object of the invention to provide new polysaccharide derivatives. It is a further object of the invention to provide derivatives of polysaccharides of the starch type useful in surgery and medicine and which have acceptable animal absorption characteristics. It is a more specific object to improve the animal absorption characteristics of substituted starch, particularly of etherified starch, which is not steam sterilized. It is a still further object to provide a polysaccharide derivative having a negligible bacteriological count without sterilisation and free from allergenic activity.

The starting materials for the present invention are substituted polysaccharides and homologues typified by substituted starch, the substitution being generally in the form of etherification or esterification at a proportion of the hydroxyl groups in the saccharide molecule. Important examples of such starting materials are any of the etherified starches produced according to U.S. Pat. No. 2,626,257.

According to the present invention a polysaccharide derivative absorbable by body tissues comprises the product of treating a substituted polysaccharide with an acid or alkaline medium and subjecting the treated material to elevated temperature until it would exhibit a reducing power, determined as herein defined, of at least 15 $R_{Cu}$ units.

Reducing power as referred to herein affords not only a criterion related to physiological acceptance of the product but also a means of distinguishing the product from the starting material as such or after sterilising by autoclaving or irradiation. It is measured as follows.

DETERMINATION OF REDUCING POWER 500 mg of the sample under test are weighed into a 150 ml Erlenmeyer flask and 25 ml of alkaline ferricyanide reagent and 5 ml of 0.2 percent glucose solution are added. The flask is placed on a water bath at 90° C. for exactly 20 minutes. This water bath is insulated and fitted with a stirrer to give uniform temperatures throughout. The flask is cooled in cold water to room temperature, 25 ml of sulphuric acid solution are added and the resulting green solution titrated dropwise with standard ceric sulphate. The end point is taken as the first distinct change in colour, i,e., from green to yellow. A blank determination is run using 5 ml of the glucose solution added to 25 ml of ferricyanide. The equivalents of ceric sulphate are converted directly to milligrams of copper and reported as $R_{Cu}$ units (mg of copper per gram of starch).

$$R_{Cu} = \frac{\text{Ml of ceric sulphate} \times \text{normality of ceric sulphate} \times 63.57}{\text{grams in sample}}$$

Reference may be made in this connection to "Reducing Power of Starches and Dextrins", F. F.Farley and R. M. Hixon, J.Ind.Eng.Chem.Anal.Ed. 13 (9), 616 (1941).

According to a preferred embodiment of the invention a modified starch derivative absorbable by body tissues comprises the product of treating an etherified vegetable starch with an acid and subjecting the acid-treated material to elevated temperature until it exhibits a reducing power of at least 15 $R_{Cu}$ units.

Sterilised products having a reducing power (before sterilisation) below 15 $R_{Cu}$ units tend to show insufficiently good animal absorption properties. In some applications there will also be a value of reducing power above which the product will have physical properties which may be less satisfactory, depending on sterilisation and the end use. Such upper limits are readily found by experiment. After sterilisation in conventional manner by gamma irradiation at 2.5 to 3.0 M rads, products having a pre-sterilisation reducing power of 15 to 45 $R_{Cu}$ units will generally be found to develop a reducing power of 65 to 100 $R_{Cu}$ units which are satisfactory limits in the case of lubricant powder for surgical gloves. Sterilisation by autoclaving, if applied, also raises the reducing power of the product of the invention to an extent predictable by experiment; mere autoclaving of the starting material, however, does not raise the reducing power to as high as 15 $R_{Cu}$ units.

The invention further proivides a method of manufacturing a polysaccharide derivative that is absorbable by body tissues, which comprises treating a substitued polysaccharide with an acid or alkaline medium and subjecting the treated material to elevated temperature until it exhibits a reducing power, determined as herein defined, of at least 15 $R_{Cu}$ units. In a preferred embodiment the method of the invention comprises treating an etherified vegetable starch with an acid and subjecting the acid-treated material to elevated temperature until it exhibits a reducing power of at least 15 $R_{Cu}$ units. The invention also extends to the step of sterilising the product of said method, for example by gamma irradiation, to obtain a sterilised modified starch derivative having a reducing power of at least 65 $R_{Cu}$ units.

The invention extends in another aspect to products treated sufficiently by the aforesaid method to impart a reducing power of more than 15 $R_{Cu}$ units (in the absence of sterilisation) to provide a bland non-toxic preparation for non-sterile uses.

In the preferred embodiments the etherified starch starting material may be made by one of the methods outlined in U.S. Pat. No. 2,626,257, most preferably the wet method, using epichlorohydrin as etherifying agent, from any of the raw starches, e.g., from corn, tapioca, sago, potato, wheat, waxy maize, sweetpotato or rice.

The treatment with acid or alkali and subsequently at elevated temperature in principle bears analogy with dextrinisation of starch, and may be performed in practice by correspondingly similar methods.

Thus a preferred embodiment of the method comprises: treating etherified starch in an aqueous slurry, obtained for instance in the conversion of starch into etherified starch, with an acid such as acetic or hydrochloric acid to obtain a pH value of 3.8 to 4.2; allowing the acidified mixture to stand, e.g., overnight, and then filtering off and drying the acidified etherified starch to a moisture content of 3 – 10 percent; treating this dried material by heating to a temperature of 80°–100° C for a period of 1 to 3 hours until the monitored reducing power reaches a value of at least 15 $R_{Cu}$ units. The thus modified starch derivative is then cooled, sieved, and preferably mixed with a flow agent such as 2 percent light magnesium oxide.

The modified polysaccharide derivatives produced according to the invention may be finally obtained or got up according to the form or prescription desired. Uses contemplated include various applications as lubricants, such as medical dusting powder particularly for surgical gloves, a lubricant for any other type of material, for example, a catheter, required to undergo temporary or prolonged contact with body tissue, a powder for plastics or rubber based materials generally used in the operating theatre area and requiring to sterilised before use, a powder lubricant as required by any disposable products used in medical care, and a release agent in manufacturing processes for medical products especially of moulded rubber or plastics. Further uses include a dressing for cotton or other materials prior to weaving, where the ultimate product may find use in surgery or medical care, a substitute for talcum powder, or an infant toilet preparation where a non-irritant powder is desirable such as in dusting female infants' bottoms. Still further uses are a diluent or vehicle for the topical application of pharmaceutical preparations in any form, or for use with any powder used during surgery and involving absorption, or in the preparation of unguents, or in tablet manufacture; and in general for any materials used in medical care in order to maintain their efficiency.

The products of the invention include in particular a dusting powder useful in all applications contemplated hitherto for etherified starch. They may be mixed with a minor proportion of a non-toxic flow agent such as nickel oxide, tin oxide or magnesium oxide or others referred to in U.S. Pat. No. 2,626,257, for instance in an amount of 0.05 to 10 percent based on the weight of the modified polysaccharide.

The invention is illustrated by the following Example of the production of modified etherified starch from starch.

EXAMPLE

In a stage preliminary to the actual process of the invention, maize starch is etherified according to the method known hitherto e.g. as described in U.S. Pat. 2,626,257, except that magnesium oxide is not added at that stage to the etherified starch product.

Maize starch is reacted with 1.5 percent aqueous epichlorohydrin solution in the presence of sodium sulphate. The temperature of the slurry is kept at 50° C for 24 hours and the pH value is maintained at 11. The slurry is then washed to remove soluble contaminants and dried first to about 40 percent moisture content and then at 50° C in an air dryer to yield etherified starch having a final moisture content of 10 percent.

The etherified starch is then acidified with dilute hydrochloric acid to a pH value of 3.8 to 4.2. The rate of modification of the etherified starch in the subsequent heating stage is strongly dependent on the pH value: too low a pH will result in conversion too rapid for convenient control, while a pH which is too high will mean that the desired modification will take many hours or, at pH values above about 6, and below about 8, will not occur.

The acidification may be performed in apparatus hitherto used for dextrinisation of starch, such as a vessel in which the charge is rotated by air-jets and the acid is injected onto it by atomisers. In a modification of the method, the acidification can be carried out in the etherification vessel.

The acidified etherified starch may be filtered if necessary. The circulating charge is raised to 70° C in the same vessel or in a screw conveyor heat exchanger until a moisture content of about 5 percent is reached, in about ½ to 1 hour. The temperature in the starch roaster is then raised to 80° to 100° C and maintained until modification is completed. Completion of the reaction is determined either by monitoring the reducing power of half-hourly withdrawn samples or by reference to a reaction time previously established in this manner. The time for reaching a specified reducing power is of the order of 1 to 5 hours in the preferred pH range, and can be readily extrapolated from readings in the earlier part of the final heating period, which provides a practically controllable reaction rate and an ample safety factor in the production scale process.

When the required reducing power is reached, roasting is stopped, followed by cooling, sieving and blending with 2 percent light magnesium oxide prior to transportation to store, e.g., by pneumatic conveyor.

By way of further illustration, the following Table shows the effect of gamma-irradiation on observed reducing power. Thus, the reducing power before irradiation is compared with the reducing power after irradiation at 2.5 to 3.0 M rads.

| Sample | Reducing power ($R_{Cu}$ Units) | |
|---|---|---|
| | Before irradiation | After irradiation |
| A | 48.0 | 102.6 |
| B | 42.9 | 96.1 |
| C | 32.7 | 93.0 |
| D | 21.9 | 87.6 |
| E | 14.3 | 78.0 |
| F | 22.0 | 78.4 |

The invention makes use of our discovery of a relationship between severity of acid-heat treatment, reducing powder and biological acceptability. The products of the invention are advantageous not only in being less irritant than gamma-irradiated etherified starch hitherto used and comparable in this respect with autoclaved etherified starch, i.e., substantially nonirritant at the reducing power specified, but they also show under microbiological examination a negligible bacteriological count even under unfavourable conditions and fail to produce allergic response.

What is claimed is:

1. A starch derivative absorbable by body tissues comprising the product of treating an etherified starch with an acid medium of pH 6 or below or with an alkaline medium of pH 8 or above and subjecting the treated material to a temperature of from about 80° to about 100° C for time sufficient to produce a product exhibiting a reducing power of at least 15 $R_{Cu}$ units.

2. The derivative of claim 1, in which said starch is a vegetable starch and said medium is acid.

3. The derivative of claim 2, wherein said starch is corn starch or maize starch.

4. The derivative of claim 2, in which the starch derivative is one in which a non-gelatinized starch has been etherified with epichlorohydrin in alkaline medium in an amount sufficient to link 2-3 percent of the hydroxyl groups.

5. The derivative of claim 4, sterilized as such or on a substrate by exposure to gamma-irradiation and thereby having a reducing power of at least 65.

6. Surgical or medical goods of plastics or rubber based materials dusted with the derivative of claim 5.

7. The derivative of claim 4, in the form of dry granules or powder.

8. A lubricant powder for surgical gloves comprising the derivative of claim 4.

9. The powder of claim 8, wherein the sterilized derivative has a reducing power of 65 to 100.

10. A method of manufacturing a starch derivative that is absorbable by body tissues, which comprises treating a substituted starch with an acid medium of pH 6 or below or with an alkaline medium of pH 8 or above and subjecting the treated material to an elevated temperature of from about 80° C to about 100° C for time sufficient to produce a product exhibiting a reducing power of at least 15 $R_{Cu}$ units.

11. The method of claim 10, further comprising the step of sterilizing the product or the product together with a substrate of exposure to gamma irradiation.

12. The method of claim 10, wherein the starch is maize starch, and the medium is aqueous acid.

13. The method of claim 12, wherein the pH value of the acid medium is 3.8 to 4.2.

14. The method of claim 13, wherein the acid is hydrochloric acid.

15. The method of claim 14, wherein said elevated temperature is maintained for 1 to 3 hours.

* * * * *

UNITED STATES PATENT AND TRADEMARK OFFICE
CERTIFICATE OF CORRECTION

PATENT NO. : 4,053,379
DATED : October 11, 1977
INVENTOR(S) : John F. Fox et al

It is certified that error appears in the above-identified patent and that said Letters Patent are hereby corrected as shown below:

In Column 6, line 31, Claim 11, "with a substrate of exposure to gamma irradiation" should read --- with a substrate by exposure to gamma irradiation ---.

Signed and Sealed this

Sixth Day of June 1978

[SEAL]

Attest:

RUTH C. MASON
*Attesting Officer*

DONALD W. BANNER
*Commissioner of Patents and Trademarks*